(12) United States Patent
Choi et al.

(10) Patent No.: US 10,251,727 B2
(45) Date of Patent: *Apr. 9, 2019

(54) METHOD AND SYSTEM FOR GENERATING A DENTAL IMPLANT SURGICAL DRILL GUIDE

(71) Applicant: ANATOMAGE Inc., San Jose, CA (US)

(72) Inventors: Woncheol Choi, San Jose, CA (US); Jia Leung Mar, Union City, CA (US)

(73) Assignee: ANATOMAGE INC., San Jose, CA (US)

( * ) Notice: Subject to any disclaimer, the term of this patent is extended or adjusted under 35 U.S.C. 154(b) by 604 days.

This patent is subject to a terminal disclaimer.

(21) Appl. No.: 14/518,735

(22) Filed: Oct. 20, 2014

(65) Prior Publication Data

US 2016/0106518 A1    Apr. 21, 2016

Related U.S. Application Data

(63) Continuation of application No. 13/311,446, filed on Dec. 5, 2011, now Pat. No. 8,892,235.

(51) Int. Cl.
| | | |
|---|---|---|
| *A61C 1/08* | (2006.01) | |
| *A01N 59/04* | (2006.01) | |
| *A01M 1/02* | (2006.01) | |
| *A61B 6/14* | (2006.01) | |

(52) U.S. Cl.
CPC ............. *A61C 1/084* (2013.01); *A01M 1/023* (2013.01); *A01N 59/04* (2013.01); *A61B 6/14* (2013.01)

(58) Field of Classification Search
CPC .. A61K 6/00; A61C 1/00; A61C 13/00; A61C 13/0004; A61C 13/12; A61C 8/00; A61C 9/0046; A61C 9/0053; A61C 13/0006; A61C 1/084; A01M 1/023; A01N 59/04; A61B 6/14
See application file for complete search history.

(56) References Cited

U.S. PATENT DOCUMENTS

| | | | | |
|---|---|---|---|---|
| 5,556,278 A | * | 9/1996 | Meitner | A61C 1/084 433/213 |
| 5,725,376 A | * | 3/1998 | Poirier | A61C 1/084 433/172 |
| 5,967,777 A | * | 10/1999 | Klein | A61C 1/084 433/75 |

(Continued)

*Primary Examiner* — Nicholas Lucchesi

(57) ABSTRACT

A method and system for producing a dental implant surgical guide is disclosed. A patient-specific virtual model is generated using image data specific to a patient and virtual dental implants. The virtual model aligns the image data with the virtual dental implants using modeling software. A virtual mold is generated from the virtual model, and a physical mold is generated from the virtual mold. The physical mold is covered with a thermoplastic sheet via a thermoforming process. Excess thermoplastic material is trimmed off after the thermoforming process to produce a thermoformed piece. Metal tubes corresponding to each the virtual dental implants are placed onto the physical mold denoting the position, trajectory, and depth of the one or more virtual dental implants. A dental implant surgical guide that contains the thermoformed piece with the one or more tubes is produced.

18 Claims, 10 Drawing Sheets

(56) References Cited

U.S. PATENT DOCUMENTS

| | | | | |
|---|---|---|---|---|
| 6,382,975 B1* | 5/2002 | Poirier | ............... | A61C 1/084 |
| | | | | 433/173 |
| 6,814,575 B2* | 11/2004 | Poirier | ............... | A61C 1/084 |
| | | | | 433/75 |
| 7,097,451 B2* | 8/2006 | Tang | ............... | A61B 17/176 |
| | | | | 433/76 |
| 7,708,557 B2* | 5/2010 | Rubbert | ............... | A61C 5/007 |
| | | | | 433/172 |
| 7,762,814 B2* | 7/2010 | van der Zel | ......... | A61C 1/084 |
| | | | | 433/201.1 |
| 8,135,412 B2* | 3/2012 | Theobold | ............ | H04W 28/00 |
| | | | | 455/434 |
| 8,135,492 B2* | 3/2012 | Yau | ............... | A61C 1/084 |
| | | | | 264/101 |
| 8,257,083 B2* | 9/2012 | Berckmans, III | .... | A61C 8/0001 |
| | | | | 433/213 |
| 2007/0154866 A1* | 7/2007 | Hall | ............... | A61C 13/0004 |
| | | | | 433/213 |
| 2008/0102415 A1* | 5/2008 | Scott | ............... | A61C 1/084 |
| | | | | 433/24 |
| 2010/0105010 A1* | 4/2010 | Mah | ............... | A61C 1/084 |
| | | | | 433/215 |

* cited by examiner

METHOD AND SYSTEM FOR GENERATING A DENTAL IMPLANT SURGICAL DRILL GUIDE

CROSS-REFERENCE TO RELATED APPLICATIONS

This application is a continuation of U.S. patent application Ser. No. 13/311,466 filed on Dec. 5, 2011, entitled "METHOD AND SYSTEM FOR GENERATING A DENTAL IMPLANT SURGICAL DRILL GUIDE," which is incorporated by reference in its entirety.

FIELD

The field of the invention relates generally to dental implant surgical guide, and more particularly to method and system for generating a dental implant surgical drill guide.

BACKGROUND

Recent technological developments in image acquisition, image planning software for dental implants, and software-based modeling allowed for a rapid, accurate, and controlled surgical planning and more accurate surgical placement of dental implants. Surgical guides, made to the shape and contour of a patient's anatomy, are used to precisely guide drilling a hole following the CT image plan's predetermined position, angle, and/or depth into a patient's jawbone. The finished hole is used for screwing in a dental implant. Such surgical planning and accurate surgical placement minimizes the patient's discomfort, reduces time for the surgical procedure, and patient's healing.

When drilling for a dental implant into the patient's jawbone, multiple drilling bits of different diameters are used in sequence to enlarge and obtain a hole with a desired size, shape, and depth. A series of drilling procedures requires meticulous planning and execution to minimize the patient's discomfort while ensuring accurate placement of the hole and avoiding vital structures such as the sinus cavity, inferior alveolar nerve and the mental foramen within the mandible. To facilitate the drilling procedures, a surgical guide maintains the position, angle, and/or depth of drilling bits while drilling. In each procedure, a slightly larger drill bit is used until the desired shape, diameter and depth of the hole is achieved.

SUMMARY

A method and system for producing a dental implant surgical guide is disclosed. A patient-specific virtual model is generated using image data specific to a patient and virtual dental implants. The virtual model aligns the image data with the virtual dental implants using modeling software. A virtual mold is generated from the virtual model, and a physical mold is generated from the virtual mold. The physical mold is covered with a thermoplastic sheet via a thermoforming process. Excess thermoplastic material is trimmed off after the thermoforming process to produce a thermoformed piece. Metal tubes corresponding to each the virtual dental implants are placed onto the physical mold denoting the position, trajectory, and depth of the one or more virtual dental implants. A dental implant surgical guide that contains the thermoformed piece with the one or more tubes is produced.

The above and other preferred features, including various novel details of implementation and combination of elements, will now be more particularly described with reference to the accompanying drawings and pointed out in the claims. It will be understood that the particular methods and apparatuses are shown by way of illustration only and not as limitations. As will be understood by those skilled in the art, the principles and features explained herein may be employed in various and numerous embodiments.

BRIEF DESCRIPTION OF THE DRAWINGS

The accompanying drawings, which are included as part of the present specification, illustrate the presently preferred embodiment of the present invention and together with the general description given above and the detailed description of the preferred embodiment given below serve to explain and teach the principles of the present invention.

Figure 1:
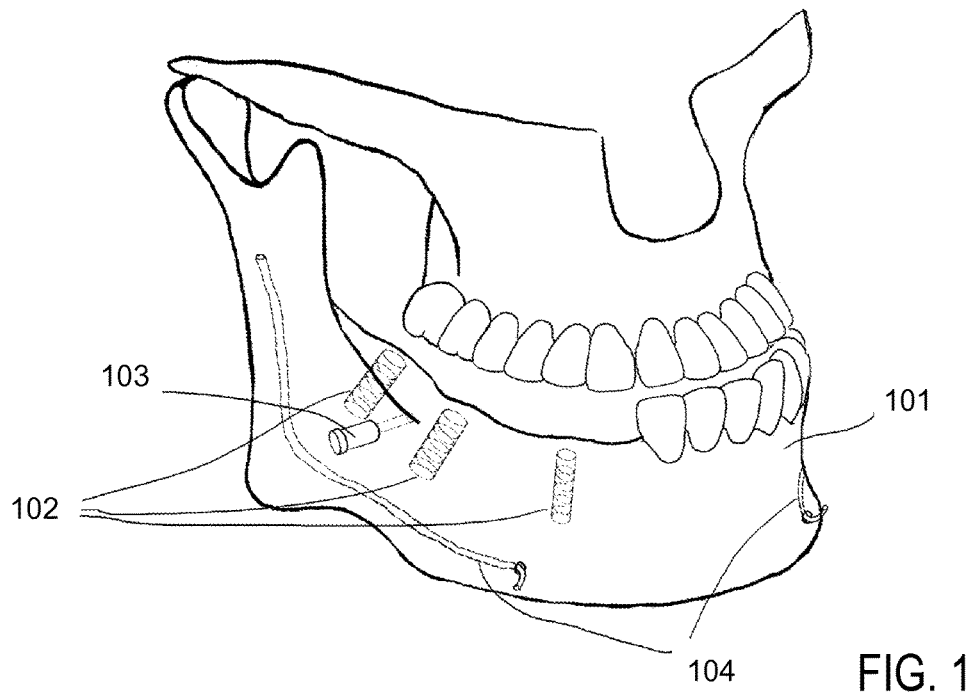
FIG. 1 illustrates an exemplary three-dimensional (3D) model, according to one embodiment.

It should be noted that the figures are not necessarily drawn to scale and that elements of structures or functions are generally represented by reference numerals for illustrative purposes throughout the figures. It also should be noted that the figures are only intended to facilitate the description of the various embodiments described herein. The figures do not describe every aspect of the teachings described herein and do not limit the scope of the claims.

DETAILED DESCRIPTION

A method and system for producing a dental implant surgical guide is disclosed. A patient-specific virtual model is generated using image data specific to a patient and virtual dental implants. The virtual model aligns the image data with the virtual dental implants using modeling software. A virtual mold is generated from the virtual model, and a physical mold is generated from the virtual mold. The physical mold is covered with a thermoplastic sheet via a thermoforming process. Excess thermoplastic material is trimmed off after the thermoforming process to produce a thermoformed piece. Metal tubes corresponding to each the virtual dental implants are placed onto the physical mold denoting the position, trajectory, and depth of the one or more virtual dental implants. A dental implant surgical guide that contains the thermoformed piece with the one or more tubes is produced.

In the following description, for purposes of clarity and conciseness of the description, not all of the numerous components shown in the schematic are described. The numerous components are shown in the drawings to provide a person of ordinary skill in the art a thorough enabling disclosure of the present invention. The operation of many of the components would be understood to one skilled in the art.

Each of the additional features and teachings disclosed herein can be utilized separately or in conjunction with other features and teachings to provide the present table game. Representative examples utilizing many of these additional features and teachings, both separately and in combination, are described in further detail with reference to the attached drawings. This detailed description is merely intended to teach a person of skill in the art further details for practicing preferred aspects of the present teachings and is not intended to limit the scope of the claims. Therefore, combinations of features disclosed in the following detailed description may not be necessary to practice the teachings in the broadest sense and are instead taught merely to describe particularly representative examples of the present teachings.

The methods presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help understand how the present teachings are practiced but are not intended to limit the dimensions and the shapes shown in the examples.

According to one embodiment, a CT image of the patient's mouth is used to plan the position and orientation of dental implants in patient's jawbone. The dental implant planning may be done in a digital realm using digital image-based planning software. The CT image data (e.g., DICOM data) is imported into the software to render a three-dimensional (3D) image of the CT image. The surgeon reviews the reconstructed 3D CT image and positions a virtual dental implant around the area of interest within the patient's mouth to determine the actual position and orientation of a dental implant. Other considerations are made during the planning procedure taking into consideration of the size of the dental implant, accessibility of the dental implant during the procedure, vital structures of the patients, etc.

A physical model of the patient's mouth is acquired via traditional dental lab techniques. The physical model is transitioned to a virtual model through various forms of software-based modeling techniques, such as CT or optical scanning in combination with 3D virtual model generating software. The virtual model is anatomically aligned to the patient CT medical image within the software. Based on the virtual model, a virtual mold that maintains the position and orientation of software planned dental implants is obtained. Using the virtual mold, the physical mold is generated, for example, via rapid prototyping techniques. After the physical mold is obtained, a thermoplastic sheet is formed over the physical mold via thermoforming techniques. Excess thermoplastic material is removed through various techniques, such as trimming, cutting, milling, and/or deburring. Metal tubes are permanently attached in the sockets of the remaining thermoplastic piece. Those metal tubes are used to guide surgical drills during a surgical procedure. After completing the thermoforming, machining, and metal tube integration procedures, a patient-specific dental implant surgical guide is obtained.

FIG. 1 illustrates an exemplary three-dimensional (3D) model of a patient's lower head bone and teeth structure, according to one embodiment. Using CT image software for dental implant planning, the patient's CT image is rendered in a 3D space. The 3D model containing the patient's bone and teeth anatomy 101 is further enhanced with the patient's marked vital structures such as inferior alveolar nerves 104 and mental foramen. Such a 3D model allows for a doctor to virtually plan dental implants 102 for safe and optimal positioning and orientation with reduced clinical risk. Anchor pin 103 for the surgical guide may be selected from the repository of implant objects in the software and included in the 3D model.

Figure 2A:
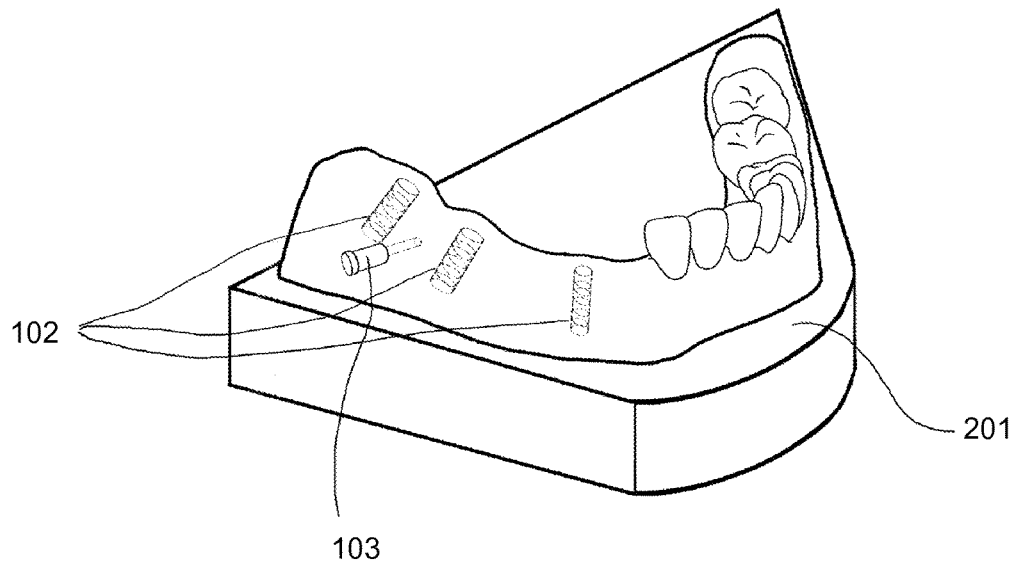
FIG. 2A illustrates an exemplary virtual model, according to one embodiment.

FIG. 2A illustrates an exemplary virtual model of patient's mouth, according to one embodiment. Virtual model 201 represents the anatomy of patient's mouth and is constructed from the patient's CT medical image. Virtual model 201 is aligned with the patient's virtual dental implants 102 and anchor pin 103 in their same position and orientation.

A physical model of the patient can be obtained in various ways. Artifacts and noise contained in the CT image may be removed by post-processing of the CT data. The enhanced quality CT data may be used to produce a physical model directly from virtual model 201. However, due to the limited resolution, artifacts and noise from the CT image with varying density, and other factors, the modeling software may not provide enough accuracy to produce a surgical guide that seats accurately on virtual model 201. In this case, a physical model is obtained from the patient, for example, by fabricating a traditional dental model from a dental impression. Various techniques are used to obtain virtual model 201 from the physical model. For example, the physical model is optically scanned or CT scanned. The modeling software uses the scan data of the physical model to generate virtual model 201. High resolution optical scanning may scan patient's mouth and directly generate virtual model 201 from the scanned data.

Virtual model 201 is loaded into the modeling software for merging with the patient's CT medical image. The operator aligns virtual model 201 to the patient CT medical image by matching the patient's identical anatomical landmarks such as teeth or gum. During the CT scan, the patient may wear a removable unit to identify the patient's anatomical landmarks. The alignment accuracy is dependent on the patient CT medical image resolution, clarity, accuracy, the resolution and accuracy of virtual model 201, and the skill of the operator. When sufficient alignment accuracy is obtained, the position and orientation of virtual dental implants 102 is transferred from the CT medical image to virtual model 201.

Figure 2B:
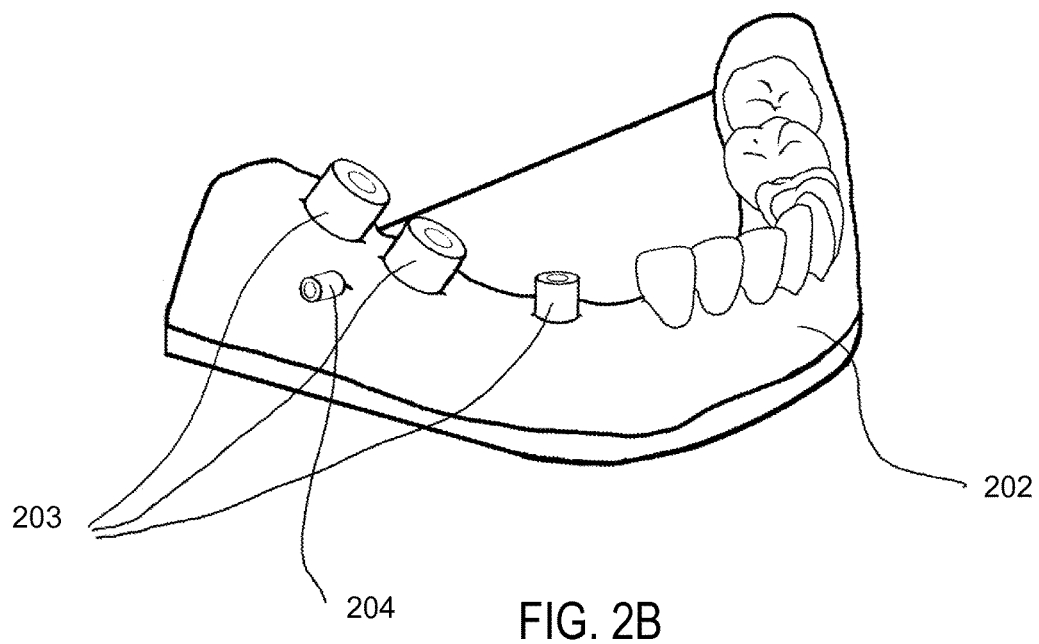
FIG. 2B illustrates an exemplary virtual mold generated from the virtual model, according to one embodiment.

FIG. 2B illustrates an exemplary virtual mold generated from the virtual model, according to one embodiment. The position and orientation of virtual dental implants 102 and anchor pin 103 are maintained by platform-socket features 203 and 204. Using the modeling software, the operator modifies the shape of virtual model 201 and creates various features including virtual mold 202 on the virtual model. In this example, these features include platform-socket features 203 and 204 that carry important dimensional information from virtual model 201 onto virtual mold 202.

Figure 2C:
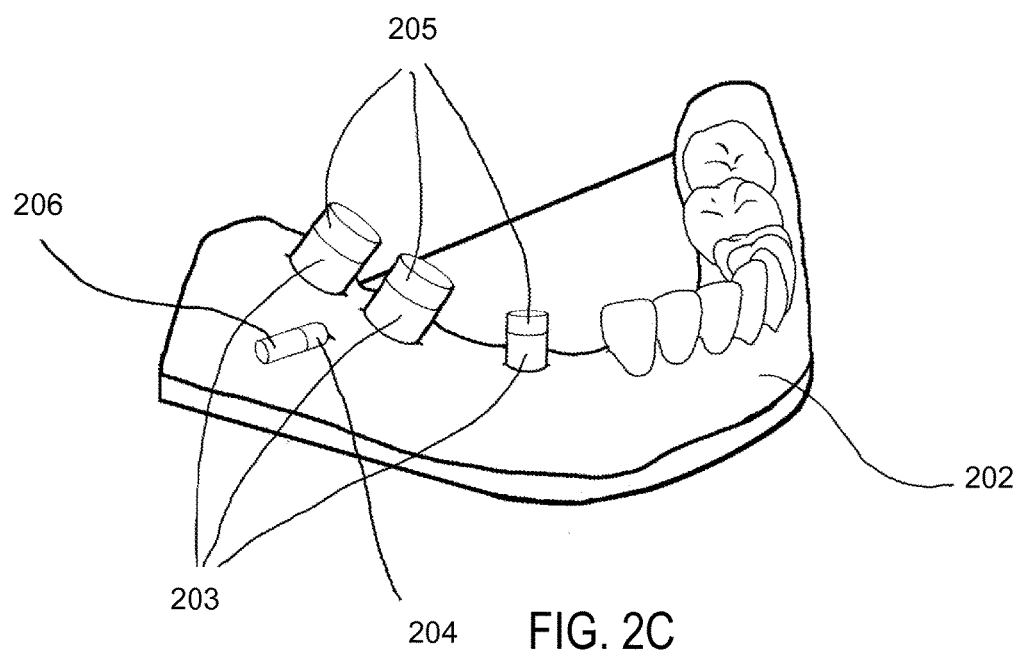
FIG. 2C illustrates an exemplary physical mold generated from a virtual mold, according to one embodiment.

FIG. 2C illustrates an exemplary physical mold generated from a virtual mold, according to one embodiment. The physical model is outfitted with features 205 and 206 that are seated against platform-socket features 203 and 204. In one embodiment, physical mold 202b is created from virtual mold 202 via rapid prototyping. Virtual mold 202 is saved in a standard file format, for example stereolithography (STL) that is compatible in majority of rapid prototyping systems. Various prototyping techniques may be used to create physical mold 202b, for example, selective laser addition (SLA), 3D printing, and 5 dimensional milling. Each prototyping means has its pros and cons in terms of accuracy, surface quality, print efficiency, cost, material properties, etc.

Figure 3A:
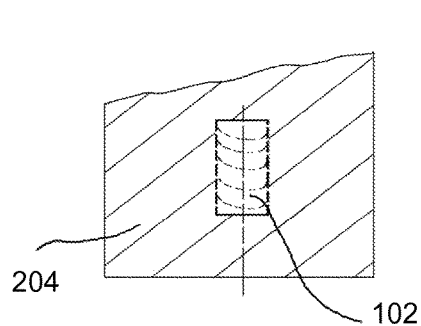
FIG. 3A illustrates a cross-section of a virtual model, according to one embodiment.
Figure 3B:
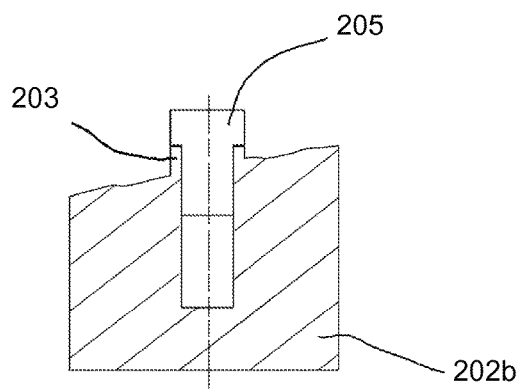
FIG. 3B illustrates a cross-section of a physical mold, according to one embodiment.

FIG. 3A illustrates a cross-section of a virtual model, according to one embodiment. FIG. 3B illustrates a cross-section of a physical mold, according to one embodiment. Physical mold 202b has the platform-socket feature 203 and part 205 seated against feature 203.

Virtual implant 102 is positioned in its doctor planned position with respect to virtual model 201. The position and orientation of virtual implant 102 is transferred to virtual mold 202 via platform-socket 203. In one embodiment, platform sockets 203 are circular and concentric about a central axis with respect to virtual implant 102 or anchor pin 103. In the modeling software, an offset is added from the top to position platform socket 203 from virtual implant 102. If additional components such as pin 205 are used in conjunction with the platform-socket 203, simply adding the offset and the length added allowing control of the implant depth from a certain offset position above virtual implant 102.

Additional features may be added to virtual mold 202. In one embodiment, filled-in negative (undercut) space is added to improve thermoform removal from virtual mold 202. Physical mold 202b created from virtual mold 202 is then prepared for thermoforming. In this case, physical components and pins 205 and 206 are fully placed within platform-sockets 203 and 204.

Thermoforming is a process in which a thermoplastic sheet is heated to a softened state and then pressed onto a mold or die. With sufficient and uniform pressure applied to the non-contact surface of the sheet, the thermoplastic sheet conforms to the outer shape of the mold or die. The thermoplastic is then cooled to obtain the shape of the mold or die. The shape of the thermoplastic sheet is maintained as long as it stays within a certain temperature range and does not experience significant forces causing physical deformation.

Figure 4B:
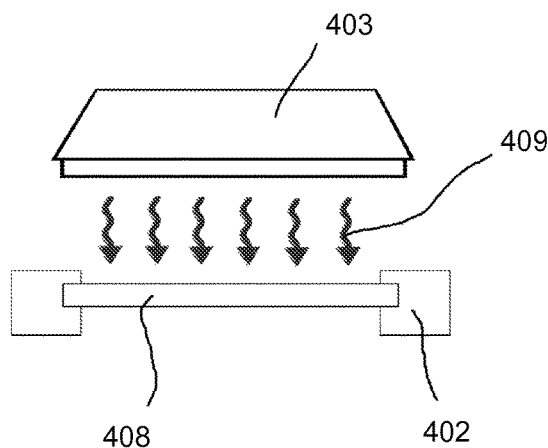
FIG. 4B illustrates a rigid state of a thermoplastic sheet.
Figure 4C:
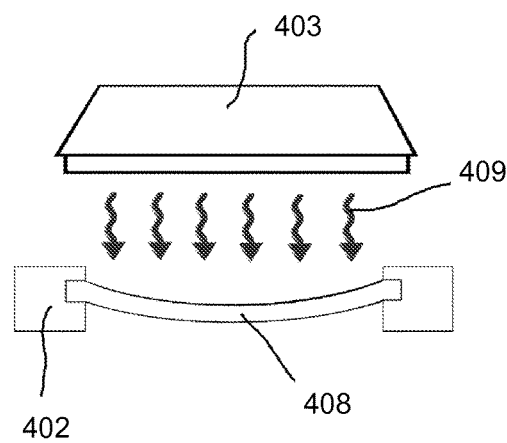
FIG. 4C illustrates a softened state of a thermoplastic sheet ready for thermoforming.
Figure 4A:
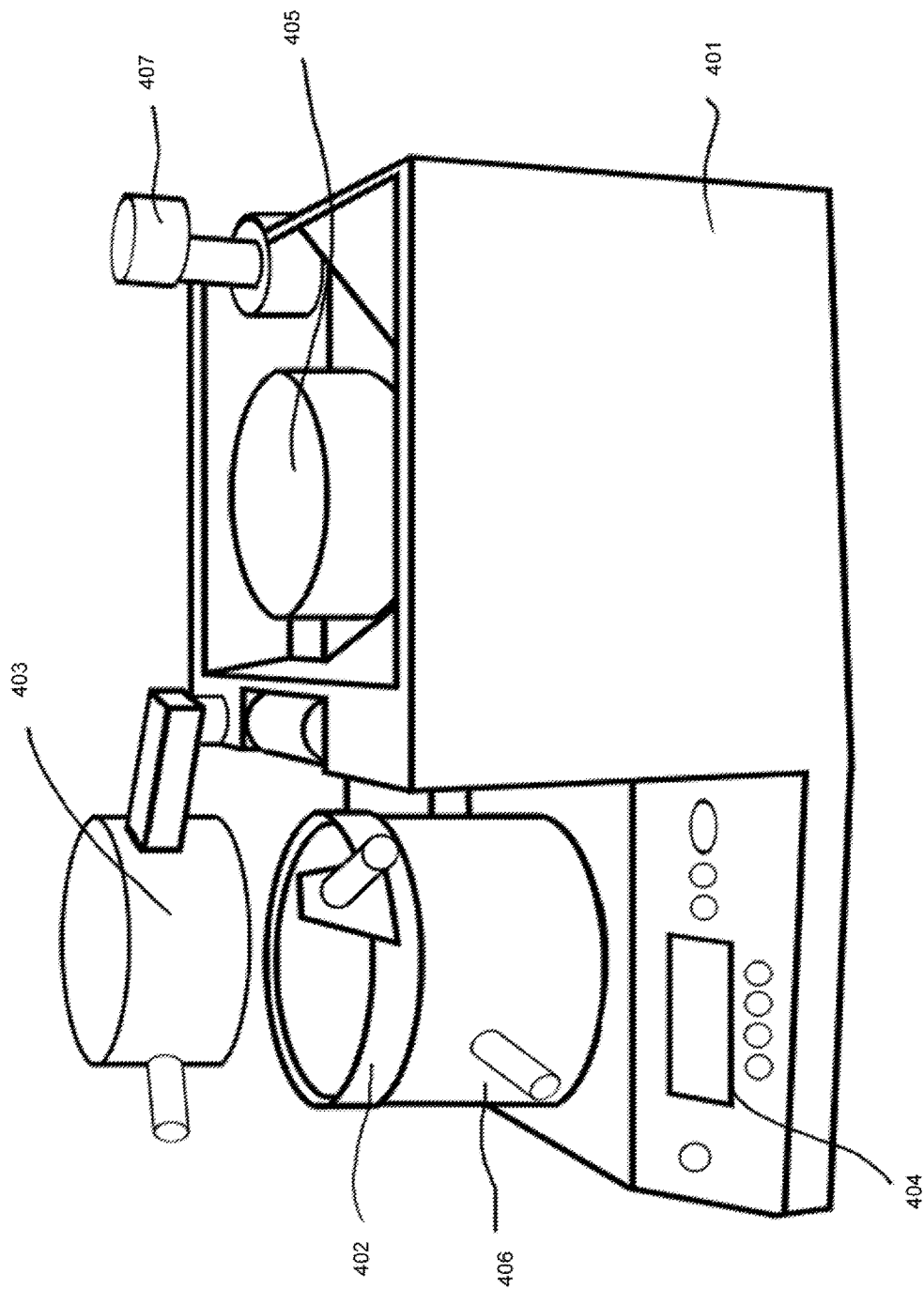
FIG. 4A illustrates an exemplary thermoforming system, according to one embodiment.

FIG. 4A illustrates an exemplary thermoforming system, according to one embodiment. Thermoforming system 401 has locking clamp 402, heating unit 403, control panel 404, platform 405, pressure chamber 406 and locking mechanism 407. A thermoplastic sheet is held by locking clamp 402. Heating unit 403 produces heat to raise the temperature and soften the thermoplastic sheet ready for thermoforming. The operator enters inputs to control panel 404 for specifying the heating time, heating power, pressure, and other control parameters for the thermoforming process. Physical mold 202b is placed upright and centered on platform 405. Thermoforming system 401 utilizes positive pressure to provide sufficient and uniform pressure onto the thermoplastic sheet for proper forming over physical mold 202b. When the thermoplastic sheet is placed over physical mold 202b, locking mechanism 407 locks pressure chamber 406 in place and signals for the unit to flood pressure chamber 406 with compressed air. Pressure chamber 406 is filled with compressed air from an external source to thermoform the thermoplastic sheet.

Thermoplastic is a type of material that loses its rigidity and changes to a softened, easily deformable state when it is exposed to a sufficient amount of heat. Thermoplastic properties vary with material properties, chemical composition, color, and thickness, etc. For the application of a dental implant surgical guide, thermoplastic material is used that is bio compatible, transparent in color and of sufficient thickness to be rigid when thermoformed. FIG. 4B illustrates a rigid state of a thermoplastic sheet. Thermoplastic sheet 408 is held by clamp 402. Heating unit 403 generates and transfers heat to the thermoplastic sheet 408. Heating unit 403 contains a high wattage heating coil. Radiant heat 409 from heating unit 403 is transferred to the thermoplastic by convection and radiation. FIG. 4C illustrates a softened state of the thermoplastic sheet ready for thermoforming.

Figure 4D:
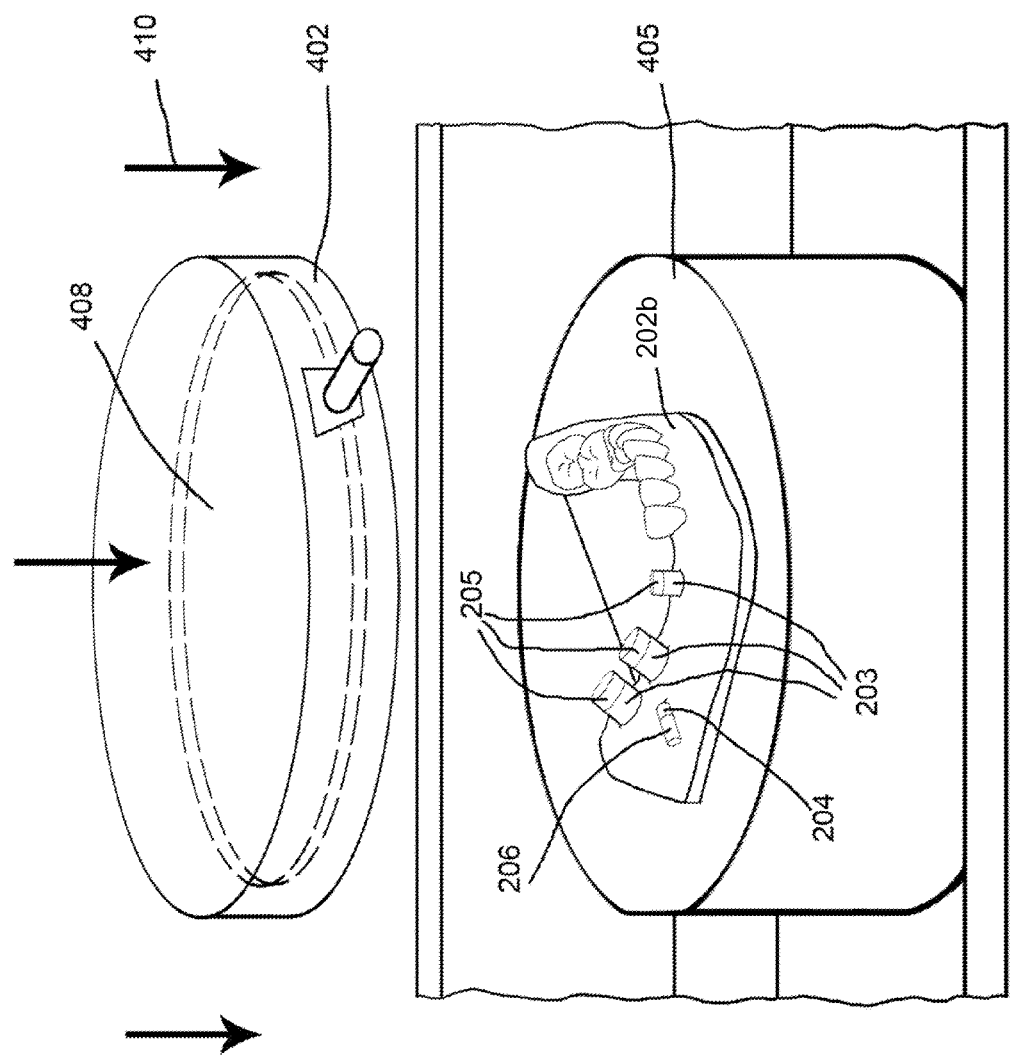
FIG. 4D illustrates an exemplary process for thermoforming preparation, according to one embodiment

FIG. 4D illustrates an exemplary process for thermoforming preparation, according to one embodiment. Thermoplastic sheet 408 is moved over physical mold 202b. To avoid thermoplastic sheet 408 reverting back to a rigid state due to rapid cooling, thermoplastic sheet 408 is quickly applied with a downward air pressure 410 onto physical mold 202b. In another embodiment, downward pressure 410 are supplied either by human operator or a machine-driven action.

Figure 4E:
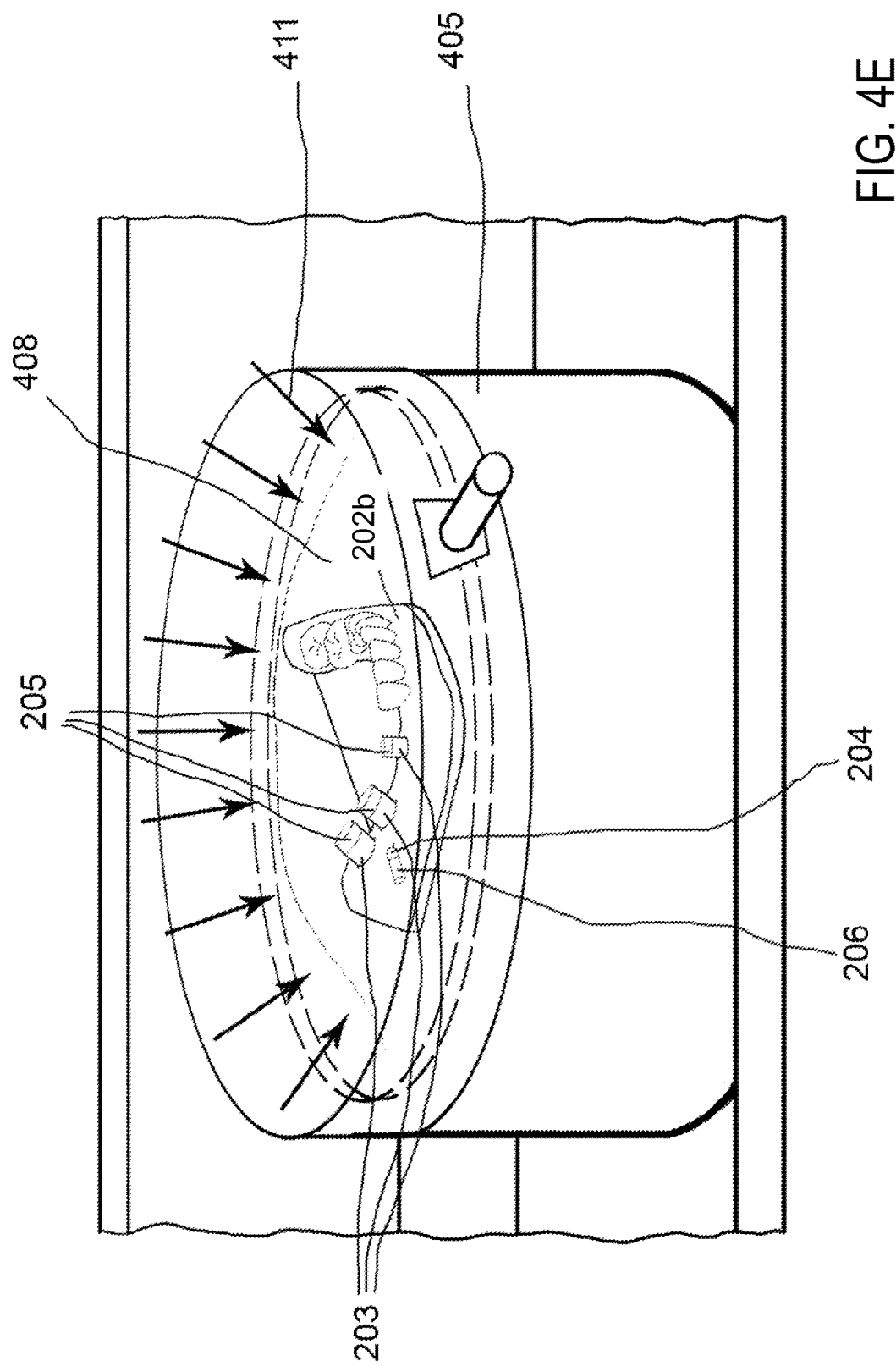
FIG. 4E illustrates an exemplary process for thermoforming, according to one embodiment.

FIG. 4E illustrates an exemplary process for thermoforming, according to one embodiment. Downward pressure 411 is applied to the non-contact side of thermoplastic sheet 408 to conform thermoplastic sheet 408 to the external contour of physical mold 202b. This thermoforming process must be performed quickly before thermoplastic sheet 408 reverts back to a rigid state due to rapid cooling. Pressure 411 can be supplied either by a human applied force to localized areas repeatedly or a systematic machine driven operation to hold thermoplastic sheet 408 down onto mold 202b. Pressure chamber 406 is filled with compressed air to apply a uniformly distributed pressure 411 over the entire non-contact side of thermoplastic sheet 408.

Figure 5A:
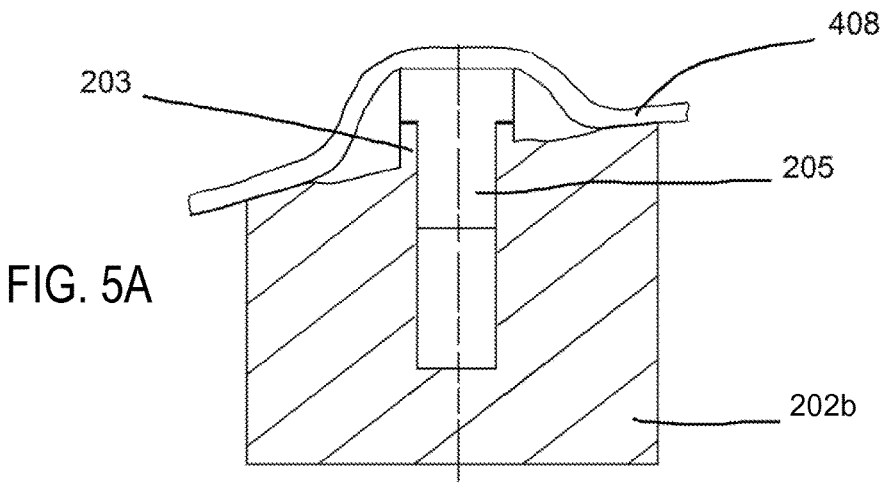
FIG. 5A illustrates a cross-section of a physical mold after thermoforming application, according to one embodiment.

FIG. 5A illustrates a cross-section of a physical mold after thermoforming application, according to one embodiment. Thermoplastic sheet 408 is applied over physical mold 202b. Thermoplastic sheet 408 has yet not sufficiently conformed to the contour of physical mold 202b. There are still negative spaces or voids between thermoplastic sheet 408 and physical mold 202b, especially in undercut or significant vertical features.

Figure 5B:
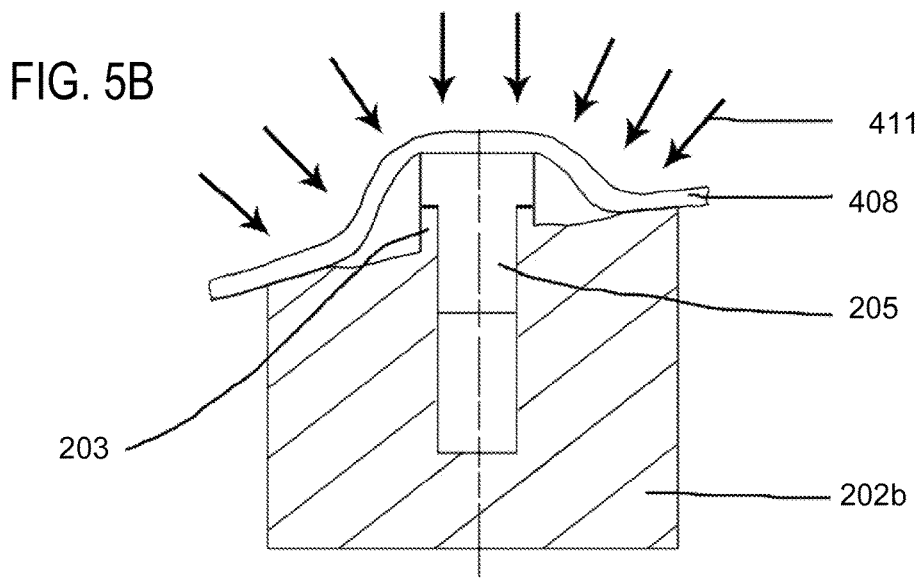
FIG. 5B illustrates the application of a uniform distributed pressure during thermoforming application, according to one embodiment.

FIG. 5B illustrates the application of a uniform distributed pressure during thermoforming application, according to one embodiment. Pressure 411 is supplied by compressed air filling pressure chamber 406 above thermoplastic sheet 408 and is applied over the non-contact side of thermoplastic sheet 408.

Figure 5C:
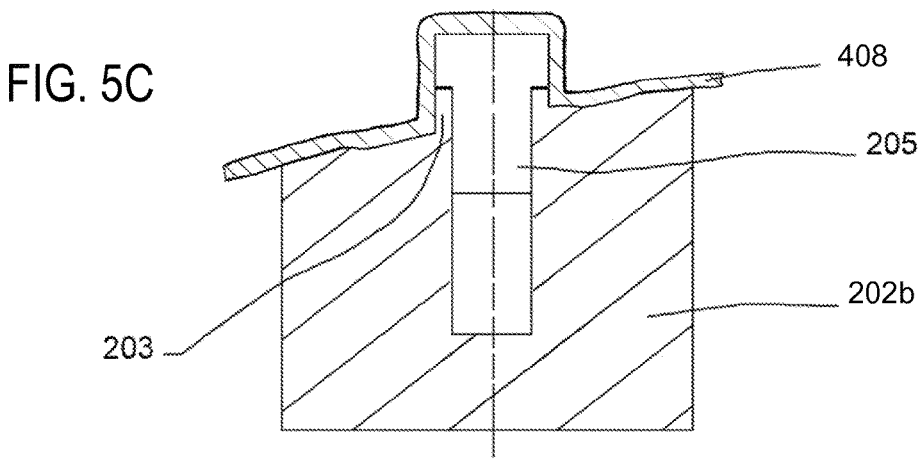
FIG. 5C illustrates an exemplary cross-section of a physical mold during thermoforming application after a uniform pressure has been applied.

FIG. 5C illustrates an exemplary cross-section of a physical mold during thermoforming application after a uniform pressure has been applied. While still in a softened state, pressure 411 forces the sheet to conform to the shape of physical mold 202b, including filling in spaces or voids between thermoplastic sheet 408 and physical mold 202b. Compressed air remains in pressure chamber 406, applying a uniform distributed pressure 411. This allows thermoplastic sheet 408 to maintain the fully conformed shape, as it cools down and transitions back to a rigid state. Once thermoplastic sheet 408 transitioned back to the rigid state, the compressed air is evacuated from pressure chamber 406, and the thermoformed mold is removed from the system.

Figure 6A:
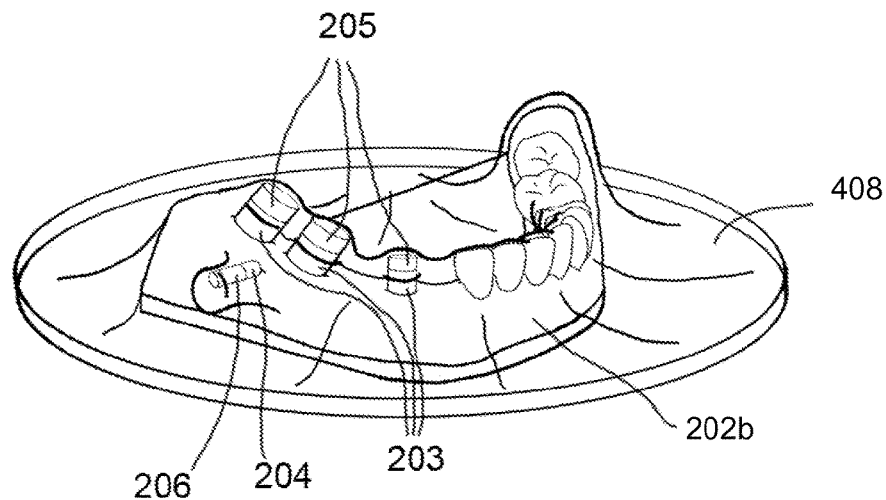
FIG. 6A illustrates an exemplary thermoformed mold, according to one embodiment.

FIG. 6A illustrates an exemplary thermoformed mold, according to one embodiment. The thermoformed mold is removed from the system for trimming. Mold 202b and features 203-206 are fully enclosed within the thermoplastic sheet. Due to the undercuts and vertical features of mold 202b, thermoformed sheet 408 cannot be removed from mold 202b before trimming.

Figure 6B:
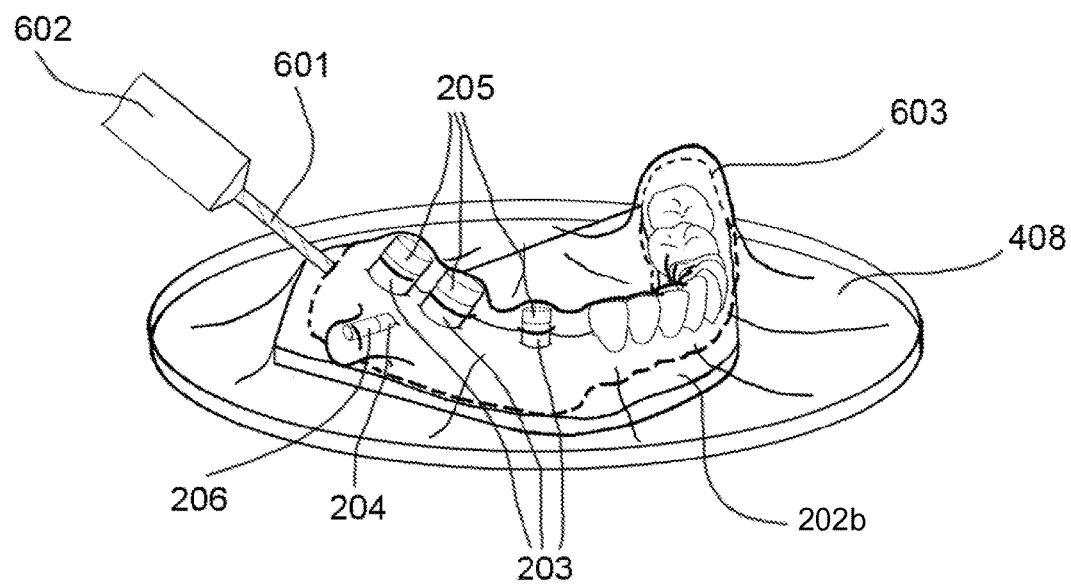
FIG. 6B illustrates an exemplary process for trimming a thermoformed thermoplastic sheet, according to one embodiment.

FIG. 6B illustrates an exemplary process for trimming a thermoformed thermoplastic sheet, according to one embodiment. Excess thermoplastic sheet is trimmed off to separate from mold 202b and obtain dental implant surgical guide 603. The trimmed portion of the thermoformed sheet forms the basis dental implant surgical guide 603. The shape of the trimmed thermoformed sheet is critical to the stability and fit quality of dental implant surgical guide 603 onto the patient, as well as obstruction to the surgeon in the localized area around the surgical site. Surgeon's preference may be taken into account during the trimming process. Based on these trimming parameters, the trimming path may be determined by an automatic software algorithm. The automatic algorithm of the trimming path may also be aided by an operator plotting a pilot path first in the software. The numerical information of the trimming path are input to an automatic cutting tool such as a six-axis robot or a computer-numerical controlled (CNC) machine to trim off thermoplastic sheet 408 as specified.

There are various methods to remove the excess off thermoplastic sheet 408. For example, thermoplastic sheet 408 is trimmed with a heat knife, cut with shears, or milled with a rotary tool. Milling with a rotary tool 602 can be accomplished either by human applied operation or a systematic machine driven operation. Forms of systematic machine driven operation include 4 or 5 axis computer numerical controlled milling system, which is programmed to follow a predetermined trim path. The trim path may be determined by a trained operator, using software, or combination of both. In this case, a specialized clamping system is used to lock the thermoformed mold into a reference position known to the milling system, so that the trim path is properly applied to mold 202b.

Drilling bit 601 is carefully selected for the milling operation. The drill bit dimensions and type are critical to the edge quality of dental implant surgical guide 603. Certain drill bits allow for more efficient cutting, to separate the excess thermoplastic material from the thermoformed piece. Post process drill bits may be further used for refining the edge, deburring, and smoothing to make the final product, dental implant surgical guide 603.

Figures 7A, 7B:
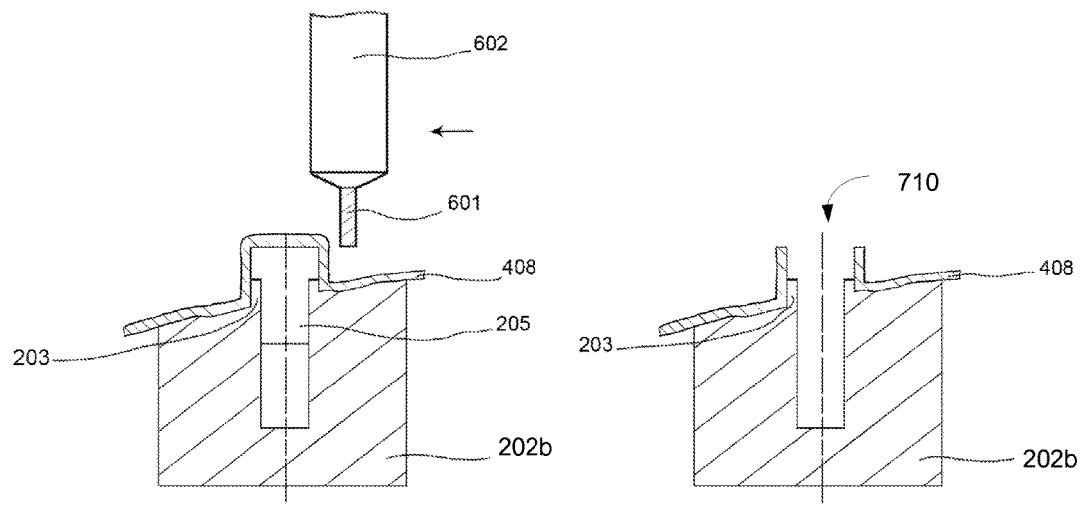
FIG. 7A illustrates an exemplary milling procedure, according to one embodiment.
FIG. 7B illustrates an exemplary trimmed thermoplastic piece with a socket receptacle flat planar surface, according to one embodiment.

FIG. 7A illustrates an exemplary milling procedure, according to one embodiment. The excess thermoplastic material is milled off around platform-socket feature 203. FIG. 7B illustrates an exemplary trimmed thermoplastic piece with a socket receptacle flat planar surface, according to one embodiment.

The excess thermoplastic material above platform-socket feature 203 is removed. The location of platform-socket feature 203 is carefully determined by the modeling software in virtual model 201 and the corresponding mold 202b with the desired position and trajectory. Rotary tool 602 is carefully used to remove the excessive thermoplastic material down to a planar surface exposing cylindrical inner diameter hole 710. Once the milling operation is complete, any detachable components, such as the part seated within the platform-socket, are removed from mold 202b. This allows for easier removal of thermoformed piece 408 from mold 202b.

Figure 7C:
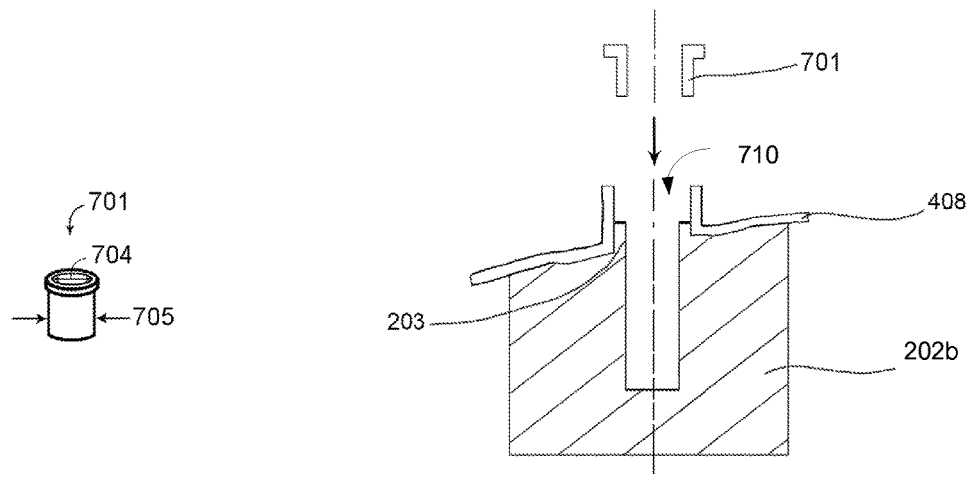
FIG. 7C illustrates an exemplary process for inserting a metal tube into a socket receptacle, according to one embodiment.

FIG. 7C illustrates an exemplary process for inserting a metal tube into a socket receptacle, according to one embodiment. Tube 701 with a fixed outer diameter 705 and inner diameter 704 is inserted into cylindrical inner diameter hole 710 of trimmed thermoformed piece 408. Tube 701 can be made of various bio compatible materials such as plastic, ceramic, or metal such as titanium, and stainless steel.

Figure 7D:
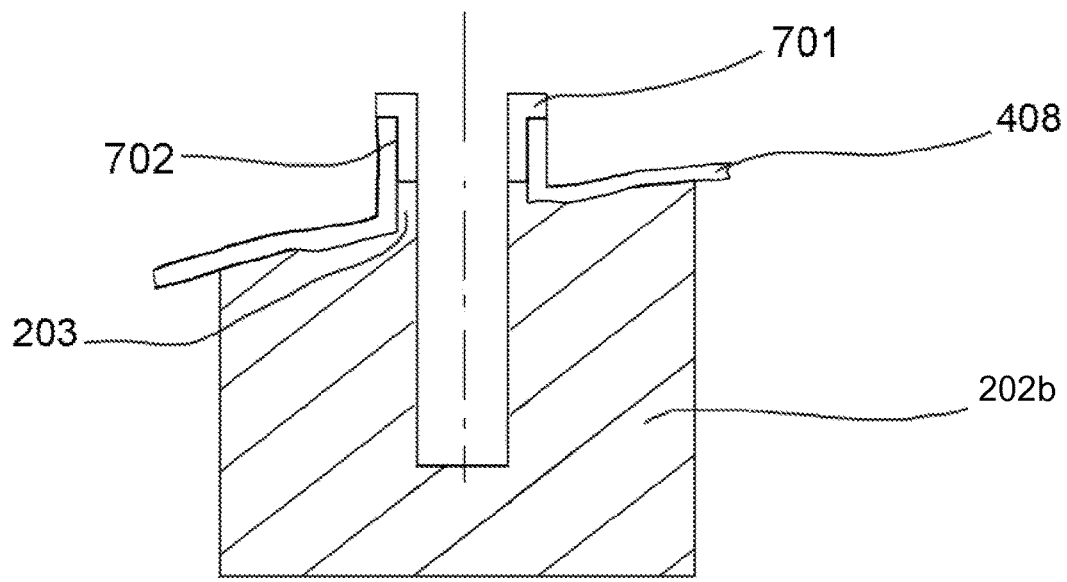
FIG. 7D illustrates a cross-section of a metal tube when inserted into the socket receptacle, according to one embodiment.

FIG. 7D illustrates a cross-section of a metal tube when inserted into the socket receptacle, according to one embodiment. Tube 701 is permanently attached to the trimmed thermoformed piece at interface boundary 702 between tube 701 and thermoformed piece 408. Various adhesives can be used to attach the tube to thermoformed piece 408, including bio compatible adhesives, cements, or resins. Ideal adhesives achieve a strong chemical bond between the thermoplastic material 408 and tube 701. Bonding strength is vital to prevent failure or premature detachment of the surgical guide from the guide due to significant shearing force. The outer surface of tube 701 may be textured with rough texture or features to promote adhesion. The flange lip of tube 701 comes in contact with the planar surface of cylindrical inner-diameter 704 of thermoformed piece 408, allowing tube 701 to be positioned at a fixed height. In addition, tube 701 may be removably attached instead of permanently attached to facilitate switching if necessary.

Tube 701 allows for the facilitation of other mating instruments or surgical drill bits to follow the constrained path of the determined implant trajectory. Since the offset position of the platform-socket 203 from the planned implant position and the fixed height of tube 701 is known, the depth from tube 701 to the planned implant position is also known. Thus, the dental implant surgical guide provides clinical information to the surgeon to achieve accurate control of position, trajectory, and depth for placing a dental implant.

Figure 8:
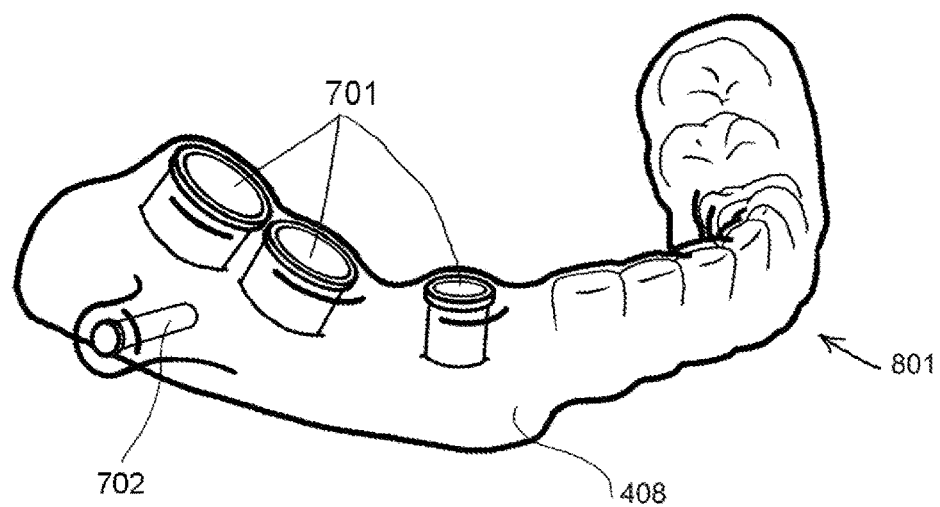
FIG. 8 illustrates an exemplary finished dental implant surgical guide, according to one embodiment.

FIG. 8 illustrates an exemplary finished dental implant surgical guide, according to one embodiment. After any post-process work and cleaning or sterilization, the manufacturing of the dental implant surgical guide 801 is produced. The finished product includes trimmed thermoformed piece 408, tubes 701 over each implant site, and if necessary tube 702 for any anchoring devices (e.g., anchor pin 103) used to stabilize guide 801 while drilling a hole.

A method and system for generating a dental implant surgical drill guide is disclosed. Although various embodiments have been described with respect to specific examples and subsystems, it will be apparent to those of ordinary skill in the art that the concepts disclosed herein are not limited to these specific examples or subsystems but extends to other embodiments as well. Included within the scope of these concepts are all of these other embodiments as specified in the claims that follow.

What is claimed is:

1. A method comprising:
receiving patient-specific image data comprising a plurality of two-dimensional images;
identifying a set of two-dimensional anatomical landmarks from the plurality of two-dimensional images of the patient-specific image data;
receiving a patient-specific virtual model;
identifying a set of three-dimensional anatomical landmarks from the patient-specific virtual model;
rendering the set of two-dimensional anatomical landmarks in a three-dimensional space;
generating a virtual mold based on the patient-specific virtual model by aligning the patient-specific image data and the patient-specific virtual model in the three-dimensional space and matching the set of two-dimensional anatomical landmarks rendered in the three-dimensional space and the set of three-dimensional anatomical landmarks; and
generating a patient-specific physical mold from the virtual mold using a rapid prototyping apparatus.

2. The method of claim 1, wherein the patient-specific image data comprises alignment data associated with a removable alignment unit, and wherein the patient- specific virtual model is aligned with the patient-specific image data using the alignment data.

3. The method of claim 1, wherein the patient-specific virtual model is obtained by a CT scan or an optical surface scan of a patient's mouth or a patient-specific physical model.

4. The method of claim 1, wherein the set of two-dimensional anatomical landmarks comprises a tooth or a gum.

5. The method of claim 1 further comprising:
placing a virtual dental implant in the patient-specific virtual model according to a virtual implant plan;
generating the virtual mold including the virtual dental implant;
generating a thermoformed piece by covering the patient-specific physical mold with a thermoplastic sheet via a thermoforming process; and
generating a dental implant surgical guide that comprises the thermoformed piece.

6. The method of claim 5, wherein the virtual mold comprises a platform and a socket that denote a position and an orientation of the virtual dental implant.

7. The method of claim 6, wherein the position and the orientation of the virtual dental implant are determined based on the virtual implant plan and are transferred to the dental implant surgical guide.

8. The method of claim 5 further comprising modifying the virtual mold by eliminating undercuts or a recessed space from the virtual model.

9. The method of claim 5, wherein the rapid prototyping apparatus employs a rapid prototyping process that is selected from a group comprising selective laser addition (SLA), 3D printing, and milling.

10. The method of claim 5, wherein the virtual model further comprises an anchor pin to stabilize the dental implant surgical guide while drilling a hole into a jawbone.

11. The method of claim 5, wherein the thermoplastic sheet is thermoformed over the patient-specific physical mold to match an outer shape of the patient-specific physical mold.

12. The method of claim 5, further comprising trimming the thermoformed piece by cutting with shears, trimming with a heat knife, or milling using a rotary tool or a computer numerical controlled rotary tool.

13. The method of claim 5, wherein a shape of the dental implant surgical guide is determined by a trained operator, software, or a combination of the both.

14. The method of claim 5, wherein the thermoformed piece includes a tube, and wherein the thermoplastic sheet is made of a bio-compatible, transparent material that provides rigidity to support the tube while drilling a hole into a jawbone.

15. The method of claim 14, wherein the tube is made of plastic, ceramic, stainless steel, or titanium.

16. The method of claim 14, wherein the tube is permanently or removably attached to the thermoformed piece.

17. The method of claim 14, wherein the tube is attached to the thermoformed piece using bio-compatible adhesives, cements, or resins.

18. The method of claim 14, wherein the tube has a surface texture or a feature to promote adhesion to the thermoformed piece.

* * * * *